United States Patent
Vakoc et al.

(10) Patent No.: US 10,653,319 B2
(45) Date of Patent: *May 19, 2020

(54) SYSTEM, APPARATUS AND METHOD FOR UTILIZING OPTICAL DISPERSION FOR FOURIER-DOMAIN OPTICAL COHERENCE TOMOGRAPHY

(71) Applicant: THE GENERAL HOSPITAL CORPORATION, Boston, MA (US)

(72) Inventors: Benjamin Vakoc, Arlington, MA (US); Meena Siddiqui, Boston, MA (US); Serhat Tozburun, Malden, MA (US)

(73) Assignee: The General Hospital Corporation, Boston, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/051,014

(22) Filed: Jul. 31, 2018

(65) Prior Publication Data

US 2019/0082962 A1    Mar. 21, 2019

Related U.S. Application Data

(63) Continuation of application No. 15/454,432, filed on Mar. 9, 2017, now Pat. No. 10,058,250, which is a
(Continued)

(51) Int. Cl.
*H01S 3/00*    (2006.01)
*H01S 3/08*    (2006.01)
(Continued)

(52) U.S. Cl.
CPC .......... *A61B 5/0066* (2013.01); *A61B 5/0075* (2013.01); *G01B 9/02004* (2013.01);
(Continued)

(58) Field of Classification Search
CPC ............ G01B 9/02005; G01B 9/02008; G01B 9/02014; G01B 9/02; H01S 3/08004;
(Continued)

(56) References Cited

U.S. PATENT DOCUMENTS 4,097,818 A * 6/1978 Manoukian .......... G02B 7/1805
                                                                 359/831
5,592,500 A    1/1997 Shirasaki
(Continued)

OTHER PUBLICATIONS

Communication pursuant to Article 94(3) EPC issued in corresponding European Application No. 14829890.4, dated Jan. 7, 2019, 5 pages.
(Continued)

*Primary Examiner* — Tuan N Nguyen
(74) *Attorney, Agent, or Firm* — Quarles & Brady LLP

(57) ABSTRACT

An apparatus can be provided which can include a laser arrangement which can be configured to provide a laser radiation, and can include an optical cavity. The optical cavity can include a dispersive optical first arrangement which can be configured to receive and disperse at least one first electro-magnetic radiation so as to provide at least one second electro-magnetic radiation. Such cavity can also include an active optical modulator second arrangement which can be configured to receive and modulate the at least one second radiation so as to provide at least one third electro-magnetic radiation. The optical cavity can further include a dispersive optical third arrangement which can be configured to receive and disperse at least one third electro-magnetic radiation so as to provide at least one fourth electro-magnetic radiation. For example, actions by the first, second and third arrangements can cause a spectral filtering of the fourth electro-magnetic radiation(s) relative to the first electro-magnetic radiation(s). The laser radiation can be associated with the fourth radiation(s), and a wavelength of
(Continued)

the laser radiation can be controlled by the spectral filtering caused by the actions by the first, second and third arrangements.

20 Claims, 9 Drawing Sheets

Related U.S. Application Data continuation of application No. 14/907,028, filed as application No. PCT/US2014/048256 on Jul. 25, 2014, now Pat. No. 9,668,652.

(60) Provisional application No. 61/858,808, filed on Jul. 26, 2013.

(51) Int. Cl.
| | |
|---|---|
| *H01S 3/106* | (2006.01) |
| *H01S 3/081* | (2006.01) |
| *A61B 5/00* | (2006.01) |
| *G01B 9/02* | (2006.01) |
| *H01S 3/067* | (2006.01) |
| *H01S 3/11* | (2006.01) |
| *H01S 5/50* | (2006.01) |

(52) U.S. Cl.
CPC ..... *G01B 9/02005* (2013.01); *G01B 9/02007* (2013.01); *G01B 9/02008* (2013.01); *G01B 9/02014* (2013.01); *G01B 9/02044* (2013.01); *G01B 9/02091* (2013.01); *H01S 3/0057* (2013.01); *H01S 3/06725* (2013.01); *H01S 3/06791* (2013.01); *H01S 3/08004* (2013.01); *H01S 3/1062* (2013.01); *H01S 3/1109* (2013.01); *H01S 3/0811* (2013.01); *H01S 5/50* (2013.01); *H01S 2301/04* (2013.01)

(58) Field of Classification Search
CPC .... H01S 3/0811; H01S 3/1109; H01S 3/1062; H01S 3/00; H01S 3/081
USPC ...................................................... 372/20, 26
See application file for complete search history.

(56) References Cited

U.S. PATENT DOCUMENTS 7,095,772 B1    8/2006  Delfyett et al.
2008/0240733 A1* 10/2008  Matsui ............ H04B 10/25133
                                                     398/193

OTHER PUBLICATIONS

Delfyett, Peter J. et al. "Chirped pulse laser sources and applications" Progress in Quantum Electronics 36 (2012) pp. 475-540, XP055342646.

Tozburun, Serhat et al. "A rapid, dispersion-based wavelength-stepped and wavelength-swept laser for optical coherence tomography" Optics Express, 2014 Optical Society of America, vol. 22, No. 3, Feb. 10, 2014, pp. 3414-3424, DOI:10.1364/OE.22.003414, XP055342180.

Lee, S. et al. "Extreme chirped pulse oscillator (XCPO) using a theta cavity design." IEEE photonics technology letters 18.7 (2006): 799-801.

Lee, S. et al. "eXtreme chirped pulse oscillator operating in the nanosecond stretched pulse regime." Optics express 16.7 (2008): 4766-4773.

Mandridis, D., et al. "Low noise chirped pulse mode-locked laser using an intra-cavity Fabry-Pérot etalon." Optics Express 19.10 (2011): 8994-8999.

* cited by examiner

SYSTEM, APPARATUS AND METHOD FOR UTILIZING OPTICAL DISPERSION FOR FOURIER-DOMAIN OPTICAL COHERENCE TOMOGRAPHY

CROSS-REFERENCE TO RELATED APPLICATION(S)

The present application is a continuation of U.S. patent application Ser. No. 15/454,432 filed Mar. 9, 2017, which is a continuation of U.S. patent application Ser. No. 14/907,028 filed on Jan. 22, 2016, which is the U.S. National Phase Application of International Patent Application No. PCT/US2014/048256 filed on Jul. 25, 2014, which claims the benefit of U.S. Provisional Application No. 61/858,808, filed Jul. 26, 2003. Each of the preceding applications is hereby incorporated by reference herein in its entirety.

STATEMENT OF FEDERAL SUPPORT

The present disclosure was made with U.S. Government support under grant number FA9550-11-1-0331 from the Department of Defense, United States Air Force, Office Of Scientific Research. Thus, the Government has certain rights to the disclosure described and claimed herein.

FIELD OF THE DISCLOSURE

The present disclosure relates to optical imaging systems, and more particularly to methods, systems and apparatus which can provide and/or utilize optical sources that have varying wavelengths for use in, e.g., Fourier-domain optical coherence tomography.

BACKGROUND INFORMATION

The potential of optical coherence tomography (OCT) configuration which can be used with a diagnostic tool/method/apparatus is capable of providing high-resolution cross-sectional images of tissue microstructure to depths of 2 mm has been well appreciated for over a decade. Many exemplary OCT systems and methods utilize a laser source with a wavelength output that changes over time. Various technologies have been described to provide such wavelength-tunable laser source. Such lasers generally include an element that selects for a specific wavelength. For example, in some optical source designs a spectral filter is incorporated into a laser cavity, and this spectral filter is configured to vary its spectral filtering properties over time [REFS]. In other designs, the laser cavity length can be modulated to affect its output wavelength [REFS]. In such designs, the rate at which the laser can change its output wavelength is a function of the rate at which the spectral filter or cavity length can be changed. In various configurations, the spectral filter or cavity length is changed through mechanical actuation, and is therefore likely limited in its rate of change by mechanical forces such as inertia.

Accordingly, there may be a need to address at least some of the above-described deficiencies.

SUMMARY OF EXEMPLARY EMBODIMENTS

Thus, to address at least such issues and/or deficiencies, exemplary embodiments of methods, systems and apparatus which can provide and/or utilize optical sources that have varying wavelengths for use in, e.g., Fourier-domain optical coherence tomography can be provided.

According to one exemplary embodiment, methods, systems and apparatus which can provide and/or utilize optical sources optical sources that can utilize, e.g., chromatically dispersive elements and/or arrangement to enable wavelength-varying optical sources. A chromatically dispersive element and/or arrangement can be configured to have differing propagation times for different wavelengths. Because the dispersive element and/or arrangement do not require a mechanical actuation, it can be used to create, facilitate and/or provide sources whose wavelength changes rapidly.

Accordingly, an exemplary apparatus can be provided which can include a laser arrangement which can be configured to provide a laser radiation, and can include an optical cavity. The optical cavity can include a dispersive optical first arrangement which can be configured to receive and disperse at least one first electro-magnetic radiation so as to provide at least one second electro-magnetic radiation. Such cavity can also include an active optical modulator second arrangement which can be configured to receive and modulate the at least one second radiation so as to provide at least one third electro-magnetic radiation. The optical cavity can further include a dispersive optical third arrangement which can be configured to receive and disperse at least one third electro-magnetic radiation so as to provide at least one fourth electro-magnetic radiation. For example, actions by the first, second and third arrangements can cause a spectral filtering of the fourth electro-magnetic radiation(s) relative to the first electro-magnetic radiation(s). The laser radiation can be associated with the fourth radiation(s), and a wavelength of the laser radiation can be controlled by the spectral filtering caused by the actions by the first, second and third arrangements.

In one exemplary embodiment of the present disclosure, the second arrangement can be and/or include an amplitude modulator, a phase modulator and/or a polarization modulator. An induced dispersion caused by the third arrangement can be approximately equal in magnitude and opposite in sign to an induced dispersion caused the first arrangement over an operating optical bandwidth of the laser arrangement. In addition, the optical cavity can include a fixed periodic spectral filter arrangement. The fixed periodic spectral filter arrangement can be or include a Fabry-Perot etalon filter.

According to another exemplary embodiment of the present disclosure, the laser radiation can have a wavelength that changes over time. For example, the actions by the first, second and third arrangements can cause the wavelength to change at a rate that is faster than 80 nm/microsec. Further or alternatively, the actions by the first, second and third arrangements can cause the wavelength to change in discrete steps. The discrete steps can be shorter than 100 nsec.

In yet another exemplary embodiment of the present disclosure, a generator can be provided which can be configured to control and/or drive the second arrangement. The generator can include and/or be a pulse generator, a pattern generator and/or a waveform generator. The first arrangement and/or a third arrangement includes a further active optical modulator arrangement that can be different from the second arrangement. At least one optical amplifier arrangement can also be provided, which can be configured to amplify the first radiation, the second radiation, the third radiation and/or the laser radiation. The optical amplifier arrangement can include or be a semiconductor amplifier, a Raman amplifier, a parametric optical amplifier and/or a fiber amplifier.

These and other objects, features and advantages of the present disclosure will become apparent upon reading the following detailed description of exemplary embodiments of the present disclosure, when taken in conjunction with the appended drawings and claims.

BRIEF DESCRIPTION OF THE DRAWINGS

Further objects, features and advantages of the invention will become apparent from the following detailed description taken in conjunction with the accompanying figures showing illustrative embodiments of the present disclosure, in which.

Figure 1:
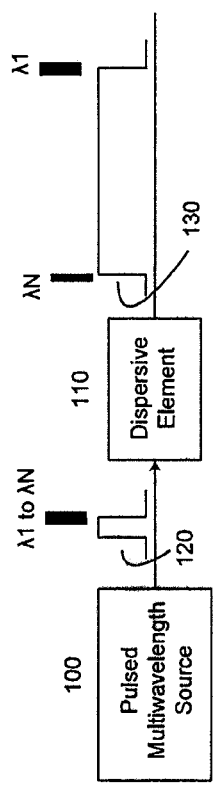
FIG. 1 is a block diagram a system which includes an optical source whose wavelength varies with time, according to an exemplary embodiment of the present disclosure.

Throughout the drawings, the same reference numerals and characters, if any and unless otherwise stated, are used to denote like features, elements, components, or portions of the illustrated embodiments. Moreover, while the subject disclosure will now be described in detail with reference to the drawings, it is done so in connection with the illustrative embodiments. It is intended that changes and modifications can be made to the described exemplary embodiments without departing from the true scope and spirit of the subject disclosure and appended claims.

DETAILED DESCRIPTION OF EXEMPLARY EMBODIMENTS

FIG. 1 shows an illustration of an optical source whose wavelength varies with time, according to an exemplary embodiment of the present disclosure. The exemplary source includes a pulsed multi-wavelength source 100 followed by a chromatically dispersive element 110. The optical pulse 120 output from the pulsed source 100 can include multiple wavelengths and can either contain a continuous spectrum of light, for example, from an amplified spontaneous light source, or can contain discrete wavelengths for example from an optical comb source. This optical pulse travels through the dispersive element 110. An output pulse 130 can be created and/or generated which can be spread in time, and each time within the pulse can include a subset of the wavelengths contained within the original pulse 120. Thus, by measuring the leading edge of the pulse, the wavelengths that have propagated faster through the system can be measured. The exemplary output pulse 130 can be used as a wavelength swept or wavelength stepped optical source pulse in the Fourier-domain OCT. The dispersive element 110 in this exemplary system can be any or a combination of, e.g., an optical fiber, a dispersion-compensating optical fiber, a photonic crystal fiber, a chirped fiber Bragg grating (FBG), a grating-based dispersive path, etc.

According to an exemplary embodiment of the present disclosure, the pulsed wavelength source 100 can comprise and/or be a continuous wave broadband light source that can be spectrally filtered (e.g., optionally amplified), and then directed to an intensity modulator to create and/or generate the pulse. Alternatively or in addition, the spectral filter can be removed if a continuous spectral source is utilized.

Figure 2A:
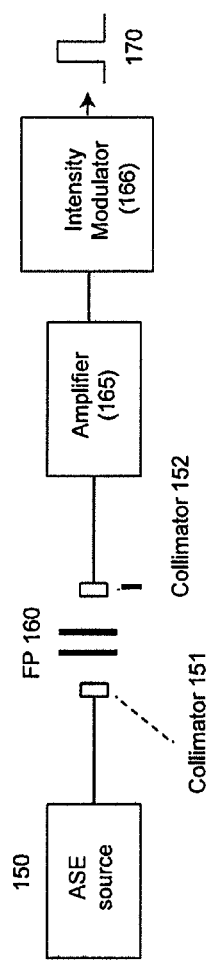
FIG. 2A is a block diagram of a pulsed wavelength source arrangement associated with or provided in the system of FIG. 1, according to an exemplary embodiment of the present disclosure.
Figure 2B:
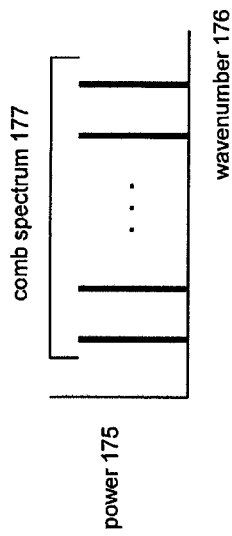
FIG. 2B is a graph of an exemplary optical comb spectrum generated by the exemplary arrangement of FIG. 2A.

An exemplary embodiment of the pulsed wavelength source according to the present disclosure is illustrated in FIG. 2A. As shown in FIG. 2A, an Amplified Spontaneous Emission (ASE) light source 150 can be used to generate the broadband continuous wave light. Such light can be collimated using two or more collimators 151, 152, and configured to be transmitted through a Fabry-Perot (FP) etalon 160 to achieve spectral filtering. This can, for example, create and/or generate an optical comb spectrum 177 which can be defined by a periodic optical power 175 versus wavenumber 176, as shown in the graph of FIG. 2B. Turning to FIG. 2A, this light can be amplified by an amplifier 165 which can be or include, e.g., a semiconductor optical amplifier, a doped-fiber amplifier, a Raman amplifier, or other optical amplifiers. Further, the light output from the amplifier 165 can be directed to an intensity modulator 166 which can be of include, for example, a Lithium Niobate modulator, among others. The resulting pulse 170 can be used as the multi-wavelength pulsed source arrangement 120 shown in FIG. 1.

Figures 3A, 3B:
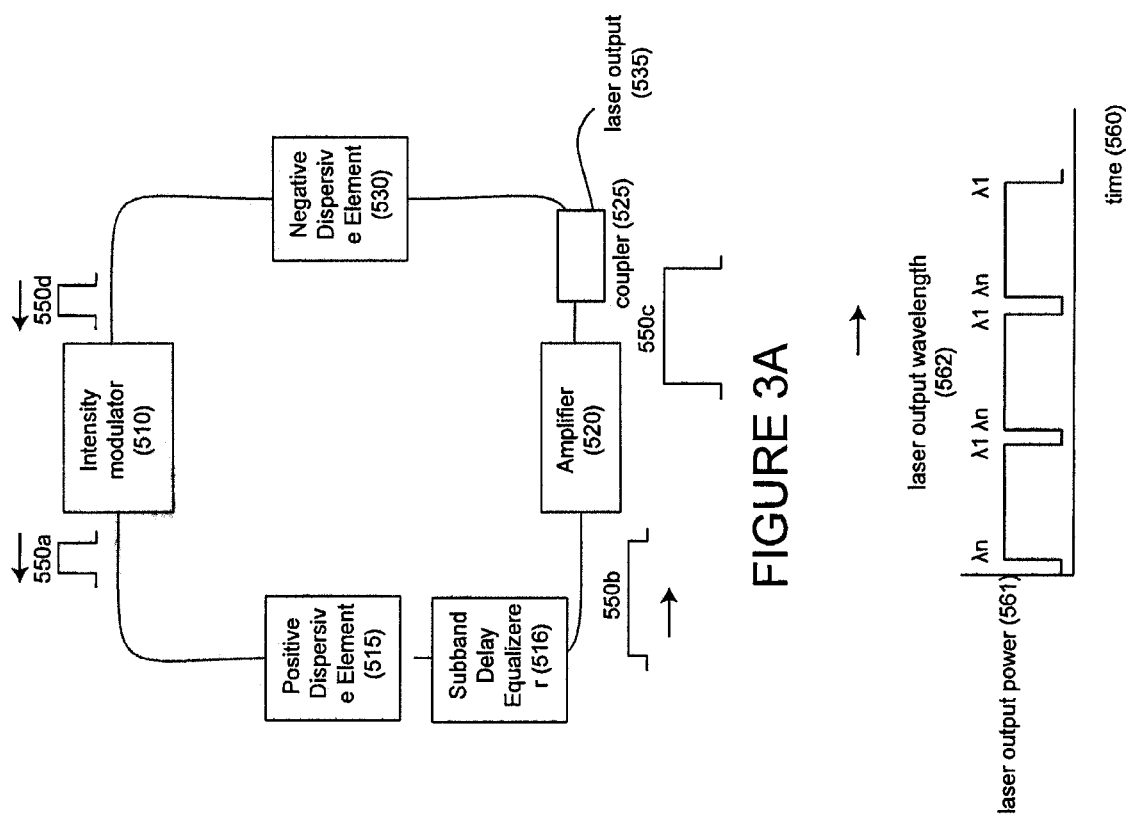
FIG. 3A is a block diagram of another system according to a further exemplary embodiment of the present disclosure in which positive and negative chromatically dispersive elements can be provided in a laser cavity to generate a wavelength varying laser output.
FIG. 3B is a plot of a resulting laser output power generated by the system of FIG. 3A versus time.

In another exemplary embodiment of the present disclosure, positive and negative chromatically dispersive elements can be provided in a laser cavity to generate a wavelength varying laser output. For example, as shown in FIG. 3A, a laser cavity can be configured and/or structured to contain or include an intensity modulator 510, a positive dispersive element/arrangement 515, an optional subband delay equalizer 516, an amplifier 520, a coupler 525, and a negative dispersive element/arrangement 530. The intensity modulator 510 can be driven to be optically transmissive for a short duration, tau, and this transmission can be repeated periodically. A generated optical pulse 550a can include multiple wavelengths, and directed to the positive dispersive element 515, where the wavelengths can, in part, be separated in time through pulse spreading effects.

If a subband delay equalizer 516 is not included in the exemplary configuration, a pulse 550b can be directed to the optical amplifier 520, where each wavelength can be amplified. This amplifier 520 could be or include, e.g., a semiconductor optical amplifier, a doped fiber amplifier, or a Raman amplifier, among others. Further, if Raman amplification is used, the amplification can be performed, in part, within a dispersive fiber that can be part of the dispersive elements/arrangements 515 or 530. The amplified light or radiation 550c can then be directed to the coupler 525, which can direct a portion to the laser output 535 and a portion to the negative dispersive element/arrangement 530. The negative dispersive element/arrangement 530 can be configured to compress such dispersed pulse to approximately its shape before it enters the positive dispersive element/arrangement 515. A compressed pulse 550d can be directed to the intensity modulator 510, and the intensity modulator 510 can be driven such that this pulse is substantially transmitted. In such exemplary configuration, the order of elements can be changed, and FIG. 2A illustrates only one exemplary ordering of various possible elements and connections. A plot 562 of a resulting laser output power 561 provided by the exemplary system of FIG. 3A versus time 560, as shown in FIG. 3B, indicates a wavelength varying nature thereof.

According to yet another exemplary embodiment of the present disclosure, the positive dispersive element/arrangement and negative dispersive elements/arrangements can be or include optical fibers which can be configured to have approximately equal and opposite chromatic dispersions across a wavelength range. In a further exemplary embodiment of the present disclosure, the subband delay equalizer 516 can be included to correct for variations in total optical propagation time through the positive dispersive element/arrangement 515 and the negative dispersive element/arrangement 530 with a wavelength.

Figure 4A:
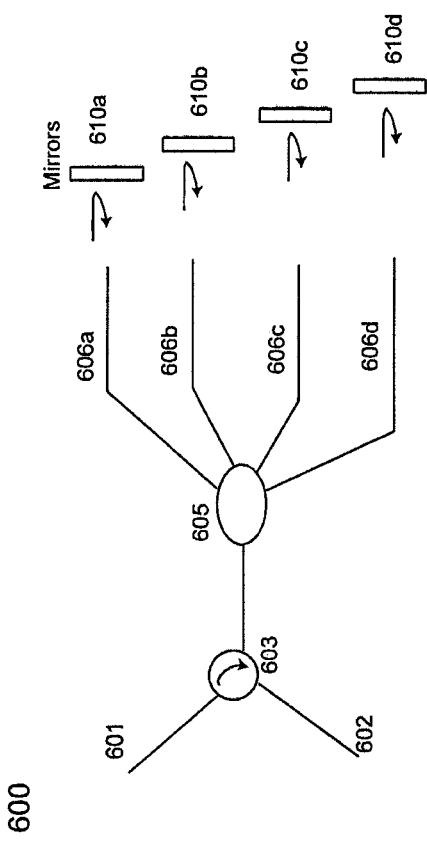
FIG. 4A is a diagram of an subband delay equalizer of the system shown in FIG. 3A, in according to yet another exemplary embodiment of the present disclosure.

In still another exemplary embodiment of the present disclosure, as shown in FIG. 4A, the subband delay equalizer 516 can constructed from a set of distinct reflective paths 600. For example, as shown in FIG. 4A, the light or other radiation can enter the subband delay equalizer at path 601, and can be directed to an optical circulator 603, where such light/radiation can be directed to a coupling arrangement 605 that can generate multiple outputs 606a, 606b, 606c, 606d. The coupling arrangement 605 can be configured to divide the input light/radiation into distinct paths according to, e.g., one or more wavelengths using, for example, wavelength-division multiplexing. Each optical path can be terminated by a reflective element/arrangement 610a, 610b, 610c, 610d (e.g., a mirror), and the optical path length between these elements/arrangements 610a, 610b, 610c, 610d and the coupling arrangement 605 can be configured to induce distinct optical propagations delays on each path. These exemplary delays can be used to adjust the overall optical propagation delay through the laser cavity for each wavelength band. Returned light/radiation can be transmitted by the optical circulator 603 to the output 602 of the subband delay equalizer 516.

Figure 4B:
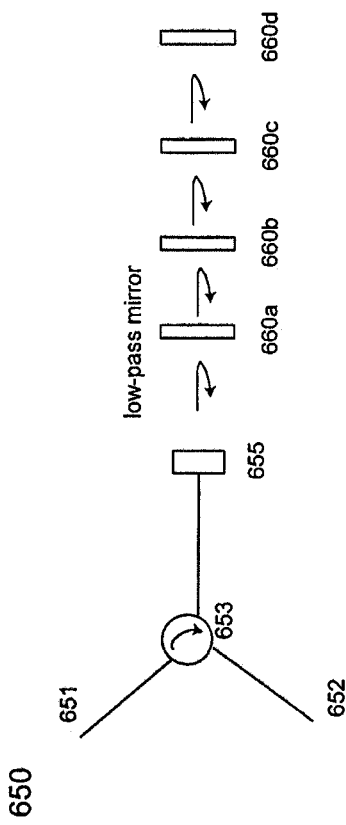
FIG. 4B is a diagram of the subband delay equalizer of the system shown in FIG. 3A, in according to a further exemplary embodiment of the present disclosure.

In a still further exemplary embodiment of the present disclosure, as shown in FIG. 4B, the subband delay equalizer 516 (which can be constructed from a set of further reflective paths 650) can comprise an input 651 that can direct the light/radiation to an optical circulator 653 which directs light to a collimator 655. The collimated beam is made to interact with a set of low-pass optical reflector arrangements 660a, 660b, 660c, 660d (e.g., mirrors) located along the beam path, facilitating wavelength bands to return to the circulator 653 with, e.g., differing optical transit times depending on which reflecting arrangement that wavelength reflected from, and where such respective reflecting arrangement is located relative to the collimator 655. The reflected light/ radiation can then be directed by the optical circulator 653 to an output 652 such that the optical delay through the subband delay equalizer 650 is wavelength dependent and configurable. The reflecting arrangements 660a, 660b, 660c, 660d can provide low-pass, band-pass or high-pass functionality, and can be or include, for example, dichroic mirrors and/or fiber Bragg gratings.

In another exemplary embodiment of the present disclosure, the exemplary source arrangement of FIG. 2A can include a spectral filter to generate a set of discrete wavelengths, rather than a continuously varying wavelength response. This spectral filter can be or include, for example, a Fabry-Perot etalon, and can be provided or positioned at any location within the laser cavity. For an exemplary operation of the exemplary source arrangement of FIG. 2A, the pulse width can be in the range of about 0.1 ns to 1 ns, and the magnitude of the dispersion induced by the positive and negative dispersive elements/arrangements can be from about 200 ps/nm to 2000 ps/nm.

Figure 5:
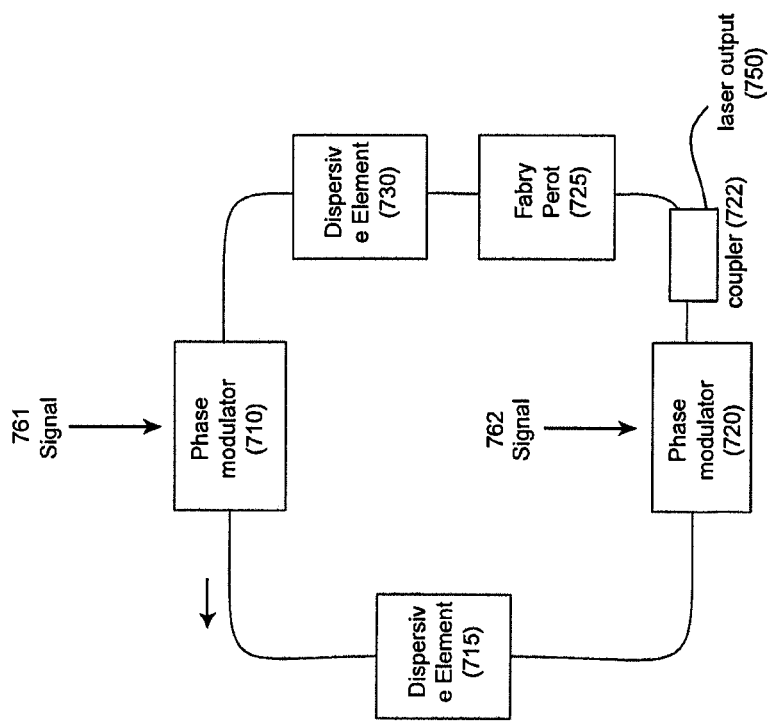
FIG. 5 is a block diagram of a source arrangement associated with or provided in the system of FIG. 1, according to still another exemplary embodiment of the present disclosure.

According to a further exemplary embodiment of the present disclosure, another exemplary source arrangement (e.g., a laser arrangement) can be provided, as illustrated in FIG. 5. The exemplary source arrangement of FIG. 5 can comprise a first optical phase modulator 710 and a second optical phase modulator 720. These exemplary phase modulators 710, 720 can be or include, for example, Lithium Niobate phase modulators. The exemplary source arrangement can also include a dispersive element/arrangement 715, an output coupler 722, a Fabry Perot etalon 725, and a compensating dispersive element/arrangement 730 with a dispersion that can be substantially equal and opposite to that provided by the dispersive element/arrangement 715.

In exemplary operation, the first phase modulator 710 can be driven by a first electrical signal 761, and the second phase modulator 720 can be driven by a second signal 762. The first light/radiation transmitted through the Fabry Perot etalon 725 can be arranged in spectral lines with a narrow instantaneous linewidth in each line. The first phase modulator 710 can induce a modulation on each line that spectrally broadens each such line. Each pulse can then travel through the dispersive element 715 to the second phase modulator 720. Because of its chromatic dispersion, each signal can reach the second phase modulator 720 at a time that is dependent on its wavelength. If the second signal 762 is opposite to the first signal 761 for a given delay, then the wavelength that has a travel-time between the first phase modulator 710 and the second phase modulator 720 can have its broadening undone, while the others will experience a further broadening by the second phase modulator 720. Thus, e.g., only the wavelength that has been re-narrowed can transmit through the Fabry Perot 725 with a high efficiency, and this wavelength would likely be that of the laser. Thus, by adjusting the first and second signals 761, 762, the lasing wavelength can be selected. If these signals are rapidly modulated, the source arrangement can be made to rapidly switch wavelengths among the transmissions modes of the Fabry Perot etalon 725, thereby achieving a wavelength-varying output at an output 750.

Figure 6:
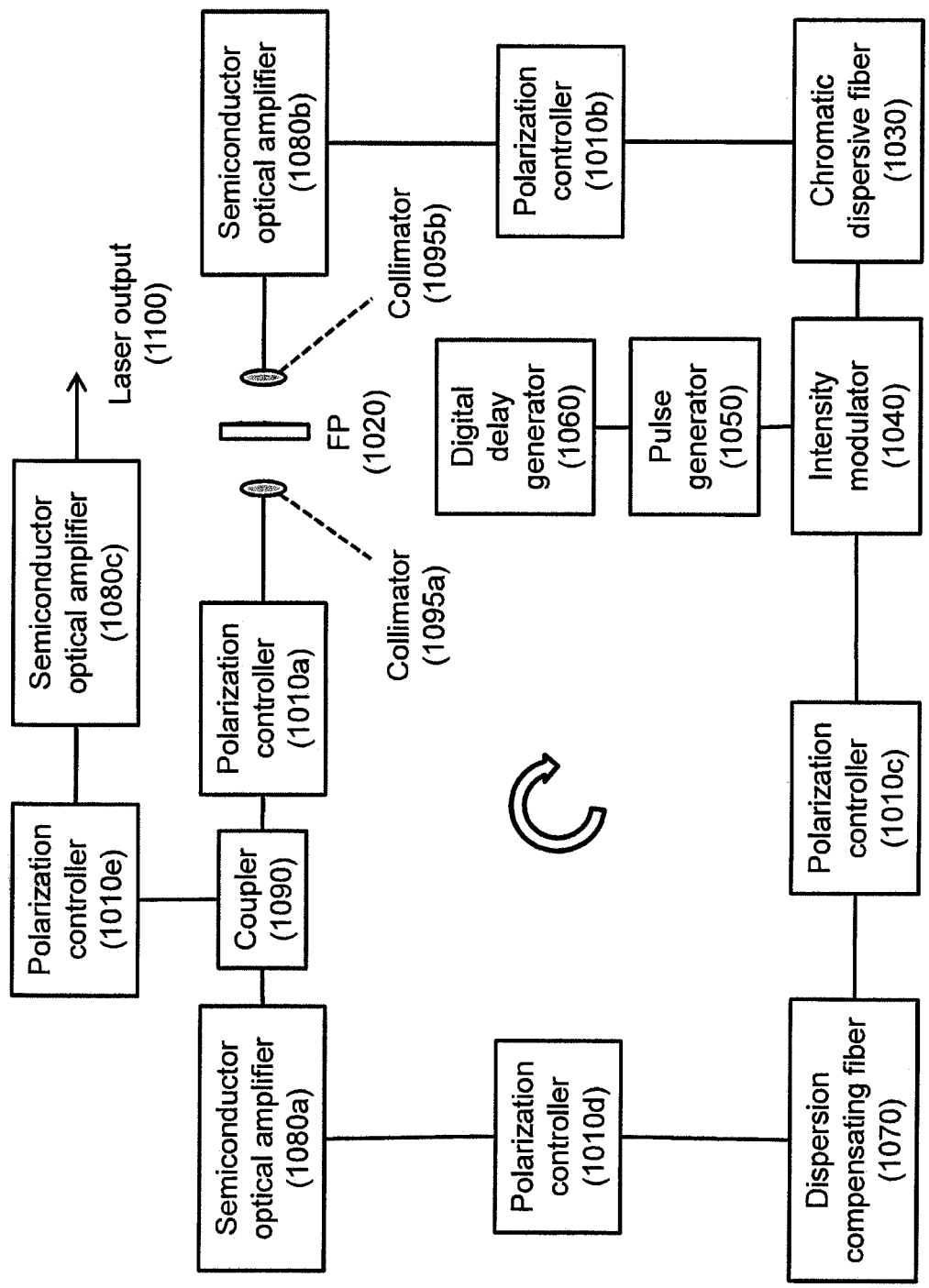
FIG. 6 is a block diagram illustrating a wavelength-stepped laser system according to another exemplary embodiment of the present disclosure.

FIG. 6 shows a block diagram of a wavelength-stepped laser source system, according to an exemplary embodiment of the present disclosure, that provides time-varying output wavelengths, e.g., substantially equally spaced in wavenumber. The exemplary source system can include a Fabry-Perot (FP) 1020 etalon with free spectral range of, e.g., about 200 GHz and finesse of about 100, approximately 39.394 km chromatic dispersive fiber (smf28e) 1030 providing approximately 680 ps/nm dispersion, a dispersion compensating fiber 1070 providing nominally approximately −680 ps/nm dispersion and designed/configured to be a dispersion slope match to the dispersive fiber 1030, approximately >30 dB extinction lithium niobate intensity modulator 1040, and two or more semiconductor optical amplifiers 1080*a*, 1080*b*. A further semiconductor optical amplifier 1080*c* outside the laser cavity can also be included and used to increase power and reduce intensity noise. A polarization state of the transmitted light (or other electro-magnetic radiation) provided via, e.g., a single mode fiber, can be altered by polarization controllers 1010*a*, 1010*b*, 1010*c*, 1010*d*, and 1010*e* for maximum transmission and/or gain. For example, a 10% tap output couple 1090 can be included that can provide the laser output (or an output of another electro-magnetic radiation). An analog pulse generator 1050 can also be provided that can be configured to generate approximately 0.50 ns full-width at half-maximum pulses. The exemplary wavelength-stepped laser source system can also include digital delay generator 1060 which can be configured to externally trigger the pulse generator 1050. Two or more collimators 1095*a*, 1095*b* can be used to generate collimated light transmitted through a Fabry-Perot (FP) 1020 etalon to achieve, e.g., a spectral spacing of about 200 GHz (1.6 nm). The wavelength-stepped source system can also include a Fabry-Perot etalon with smaller free spectral range that can be in the range of about 0.1 GHz to 10,000 GHz. Additional dispersive elements can be included in the cavity, e.g., to improve the matching between the positive and negative dispersive arrangements. Additionally, other dispersive elements, such as, e.g., chirped fiber Bragg gratings, can be used to provide positive or negative dispersion.

Figure 7:
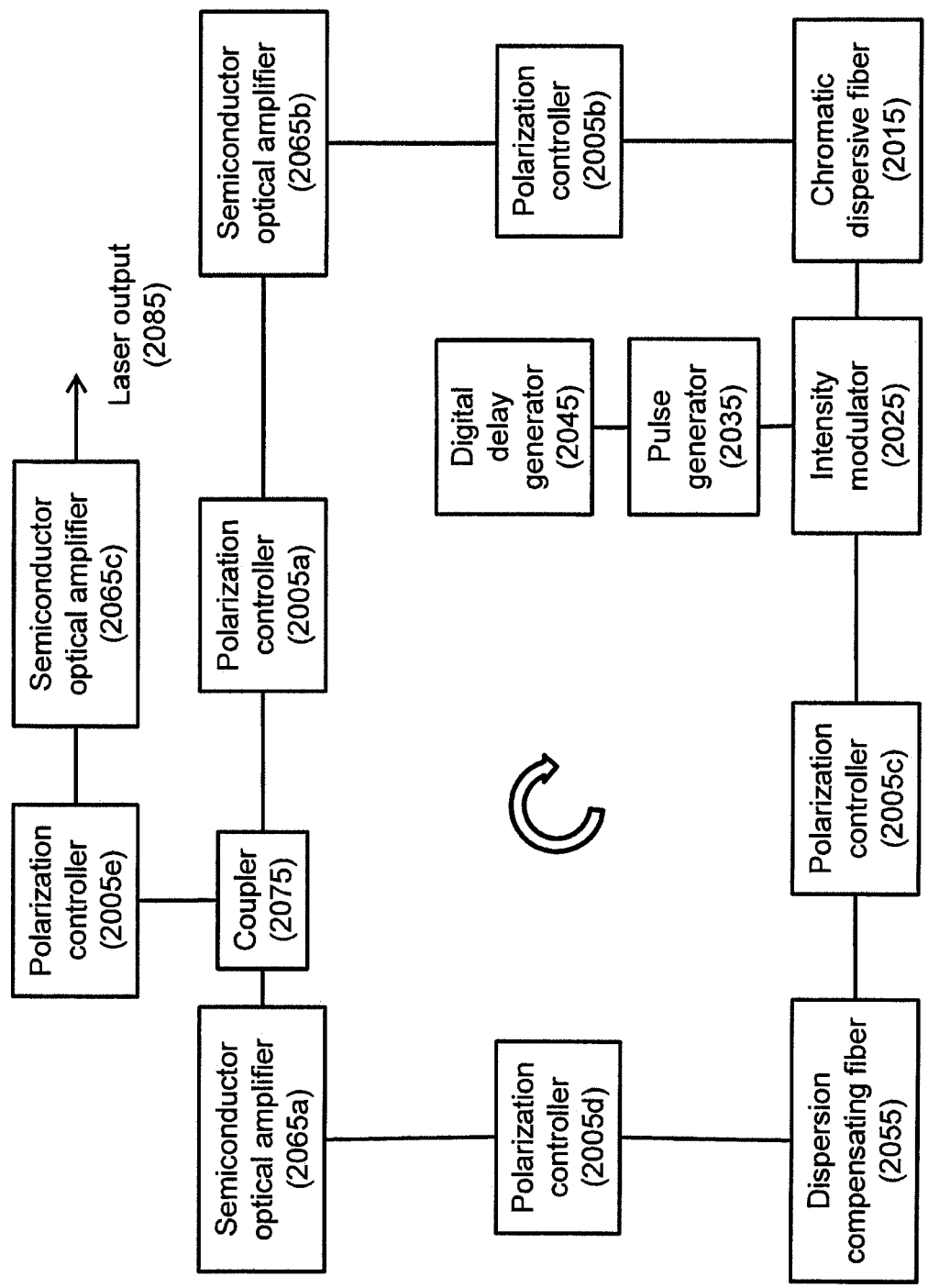
FIG. 7 is a block diagram illustrating the wavelength-swept laser system according to still another exemplary embodiment of the present disclosure.

According to yet another embodiment of the present disclosure, it is also possible to provide a rapid wavelength-swept source system for effectuating a Fourier-domain Optical Coherence Tomography. For example, a removal of the intracavity Fabry-Perot etalon can facilitate a continuous spectral operation. FIG. 7 shows a block diagram of the wavelength-swept laser source system that provides time-varying output wavelengths continuously in wavenumber according to a further exemplary embodiment of the present disclosure. The exemplary source system illustrated in FIG. 7 can include a 39.394 km chromatic dispersive fiber (smf28e) 2015, a dispersion compensating fiber 2055 designed and/or configured to be dispersion slope match to a chromatic dispersive fiber 2015, a >30 dB extinction lithium niobate intensity modulator 2025, and two semiconductor optical amplifiers 2065*a*, 2065*b*. For example, approximately 10% tap output couple 2075 can provide the laser output (or output of another electro-magnetic radiation). Another semiconductor optical amplifier 2065*c* outside the laser cavity can be provided and utilized to increase power and reduce intensity noise. A polarization state of the transmitted light (or other electro-magnetic radiation) through, e.g., a single mode fiber can be altered by polarization controllers 2005*a*, 2005*b*, 2005*c*, 2005*d*, and 2005*e* for maximum transmission and gain. An analog pulse generator 2035 can be used to generate approximately 0.50 ns full-width at half-maximum pulses. A digital delay generator 2045 can be used to externally trigger the pulse generator 2035.

Figure 8:
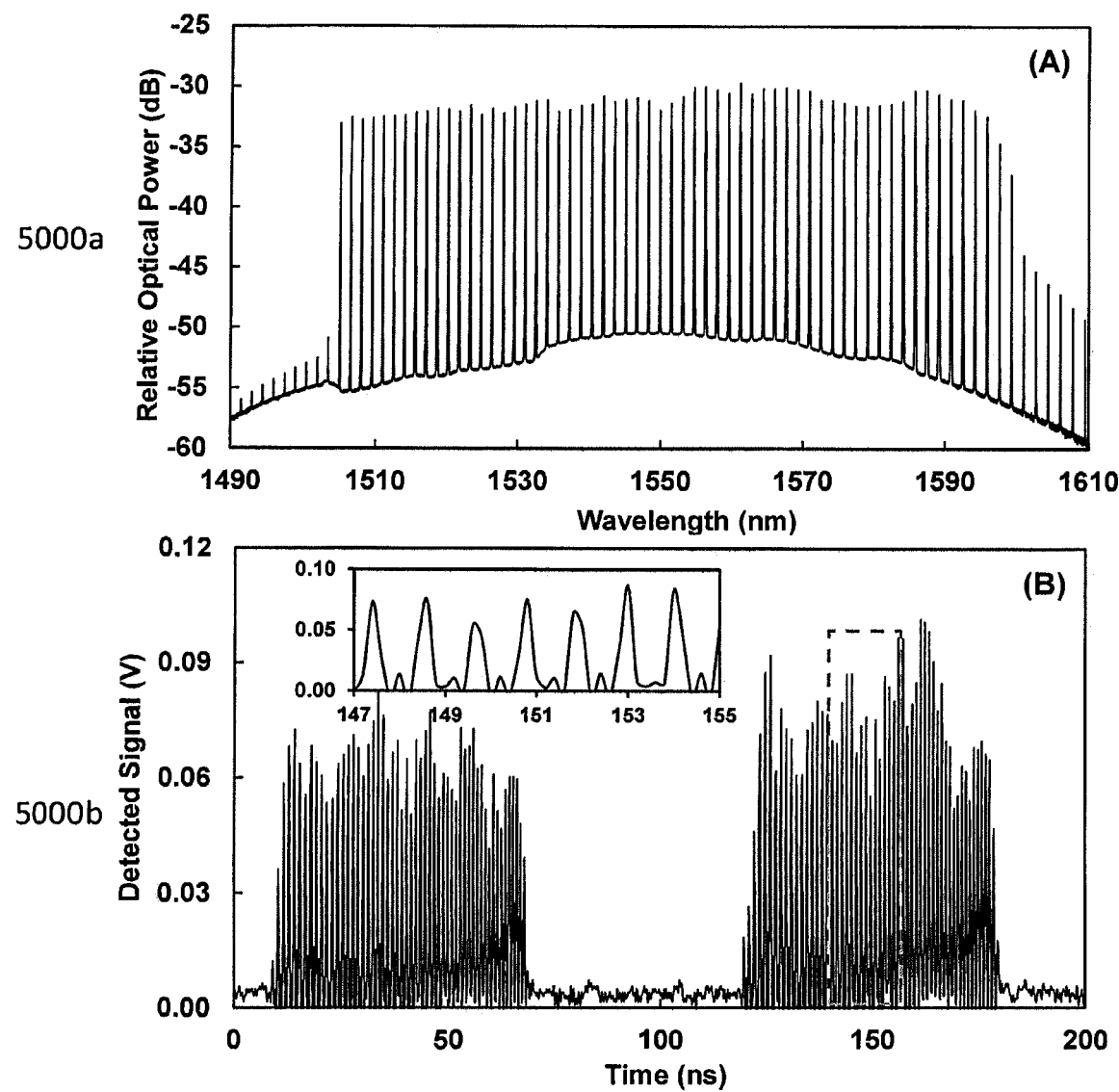
FIG. 8 panels A and B are graphs illustrating measured laser outputs of the exemplary wavelength-stepped laser in the spectrum domain and the time domain, respectively, at different mirror distance in air.

The output spectrum of the wavelength-stepped laser system indicates a spectral comb structure forced by the 200 GHz (1.6 nm) free spectral range Fabry-Perot etalon, as shown in FIG. 8 panel A in an exemplary graph 5000*a*. For example, the lasing bandwidth can be measured to be about 94 nm. The laser output (or other electro-magnetic radiation) in the time domain at a repetition rate of over 9 MHz is shown in FIG. 8 panel B as a graph 5000*b*. Such exemplary rate can be increased up to 100 MHz with suitable electronic drive signals. The exemplary generation of temporally separated optical pulses for each wavelength is also shown in panels A and B of FIG. 8 with, e.g., approximately 2 GHz receiver bandwidth limitations. The exemplary source system can be operated at, e.g., about 54% duty cycle. The exemplary duty cycle can be increased/decreased by changing the pulse generation rate with components of the digital delay generator 1060 and/or the pulse generator 1050 of FIG. 6. The illustrated source system can be run at, e.g., approximately 20 MHz repetition rates with a duty cycle near 100%. The exemplary operation can also be run at other repetition rates, as should be understood by those having ordinary skill in the art.

Figure 9:
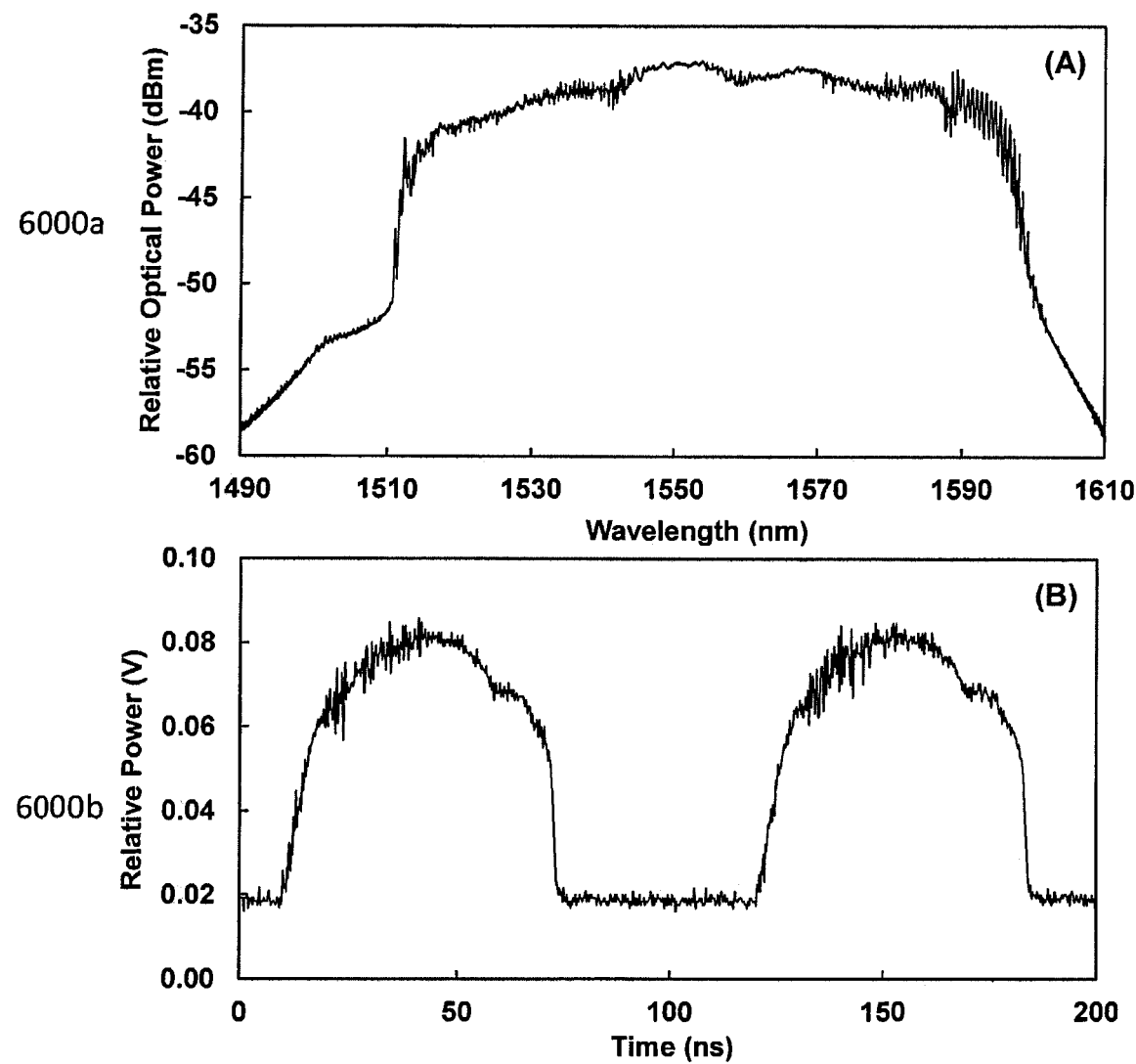
FIG. 9 panels A and B are graphs illustrating representative laser outputs of the exemplary wavelength-swept laser in the spectrum domain and the time domain, respectively at different mirror distance in air.

FIG. 9 panels A and B illustrate exemplary graphs providing exemplary results that characterize the exemplary wavelength-swept laser source system of FIG. 7. For example, FIG. 9 panel A shows an exemplary optical spectrum-tracing graph 6000*a* illustrating an optical bandwidth of, e.g., about 87 nm. This exemplary spectral bandwidth can be increased and/or decreased by, e.g., adjusting the gain medium, duty cycle of the intensity modulator, and/or the matching of the dispersion fibers 2015 and 2055 shown in FIG. 7. FIG. 9 panel B shows an exemplary graph 6000*b* of an expected continuous shape of the exemplary output of the exemplary laser system, e.g., with about 9 MHz repetition rate.

The foregoing merely illustrates the principles of the disclosure. Various modifications and alterations to the described embodiments will be apparent to those skilled in the art in view of the teachings herein. Indeed, the arrangements, systems and methods according to the exemplary embodiments of the present disclosure can be used with and/or implement any OCT system, OFDI system, SD-OCT system or other imaging systems, and for example with those described in International Patent Application PCT/US2004/029148, filed Sep. 8, 2004 which published as International Patent Publication No. WO 2005/047813 on May 26, 2005, U.S. patent application Ser. No. 11/266,779, filed Nov. 2, 2005 which published as U.S. Patent Publication No. 2006/0093276 on May 4, 2006, and U.S. patent application Ser. No. 10/501,276, filed Jul. 9, 2004 which published as U.S. Patent Publication No. 2005/0018201 on Jan. 27, 2005, and U.S. Patent Publication No. 2002/0122246, published on May 9, 2002, the disclosures of which are incorporated by reference herein in their entireties. It will thus be appreciated that those skilled in the art will be able to devise numerous systems, arrangements and methods which, although not explicitly shown or described herein, embody the principles of the disclosure and are thus within the spirit and scope of the present disclosure. It should be understood that the exemplary procedures described herein can be stored on any computer accessible medium, including a hard drive, RAM, ROM, removable disks, CD-ROM, memory sticks, etc., and executed by a processing arrangement and/or computing arrangement which can be and/or include a hardware processors, microprocessor, mini, macro, mainframe, etc., including a plurality and/or combination thereof. In addition, certain terms used in the present disclosure, including the specification, drawings and claims thereof, can be used synonymously in certain instances, including, but not limited to, e.g., data and information. It should be understood that, while these words, and/or other words that can be synonymous to one another, can be used synonymously herein, that there can be instances when such words can be intended to not be used synonymously. Further, to the extent that the prior art knowledge has not been explicitly incorporated by reference herein above, it can be explicitly incorporated herein in its entirety. All publications referenced herein can be incorporated herein by reference in their entireties.

What is claimed is:

1. An apparatus, comprising:
a laser to provide a laser radiation,
the laser including an optical cavity comprising:
a first dispersive element which receives and disperses a first electro-magnetic radiation and outputs a second electro-magnetic radiation,
a first phase modulator which receives and modulates the second electro-magnetic radiation and outputs a third electro-magnetic radiation,
a second dispersive element that receives and disperses the third electro-magnetic radiation and outputs a fourth electro-magnetic radiation, and
a second phase modulator which receives and modulates the fourth electro-magnetic radiation and outputs a fifth electro-magnetic radiation,
the laser radiation being based on at least one of:
the first electro-magnetic radiation,
the second electro-magnetic radiation,
the third electro-magnetic radiation,
the fourth electro-magnetic radiation, or
the fifth electro-magnetic radiation.

2. The apparatus of claim 1, wherein the optical cavity further comprises a coupler which receives and splits the fifth electro-magnetic radiation into a first portion and a second portion,
wherein the first portion is output by the coupler as a sixth electro-magnetic radiation, and
wherein the second portion is output by the coupler as the laser radiation.

3. The apparatus of claim 2, wherein the optical cavity further comprises a fixed periodic spectral filter,
wherein the fixed periodic spectral filter receives and filters the sixth electro-magnetic radiation and outputs a seventh electro-magnetic radiation,
wherein the first electro-magnetic radiation comprises the seventh electro-magnetic radiation.

4. The apparatus of claim 3, wherein the first phase modulator is controlled by a first control signal,
wherein the first control signal has a first state that causes the first phase modulator to spectrally broaden the second electro-magnetic radiation and a second state opposite the first state that causes the first phase modulator to spectrally narrow the second electro-magnetic radiation, and
wherein the second phase modulator is controlled by a second control signal,
wherein the second control signal has a third state that causes the second phase modulator to spectrally broaden the fourth electro-magnetic radiation and a fourth state opposite the third state that causes the second phase modulator to spectrally narrow the fourth electro-magnetic radiation.

5. The apparatus of claim 4, wherein the seventh electro-magnetic radiation output by the fixed periodic spectral filter comprises a plurality of spectral lines including a particular spectral line,
wherein, when the first control signal is in the first state, the particular spectral line is spectrally broadened by the first phase modulator, and
wherein, when the second control signal is in the fourth state, the particular spectral line is spectrally narrowed by the second phase modulator.

6. The apparatus of claim 5, wherein the particular spectral line is received and filtered by the fixed periodic spectral filter based on being spectrally narrowed by the second phase modulator.

7. The apparatus of claim 6, wherein the particular spectral line travels from the first phase modulator and reaches the second phase modulator after a delay time,
wherein the particular spectral line has a particular wavelength, and
wherein the delay time between the first control signal and the second control signal is based on selecting the particular spectral line having the particular wavelength.

8. The apparatus of claim 7, wherein the delay time between the first control signal and the second control signal is changed to another delay time to select another spectral line of the plurality of spectral lines,
wherein the other spectral line has another wavelength different from the particular wavelength.

9. The apparatus of claim 8, wherein the other spectral line is received and filtered by the fixed periodic spectral filter based on being spectrally narrowed by the second phase modulator.

10. The apparatus of claim 1, further comprising an optical amplifier which receives an input electro-magnetic radiation and emits an output electro-magnetic radiation,
wherein the output electro-magnetic radiation comprises at least one of a source electro-magnetic radiation or an amplification of the input electro-magnetic radiation, and
wherein the output electro-magnetic radiation is combined with at least one of:
the first electro-magnetic radiation,
the second electro-magnetic radiation,
the third electro-magnetic radiation,
the fourth electro-magnetic radiation, or
the fifth electro-magnetic radiation.

11. A method, comprising:
providing, using a laser, a laser radiation,
the laser including an optical cavity comprising a first dispersive element, a first phase modulator, a second dispersive element, and a second phase modulator;
the first dispersive element receiving and dispersing a first electro-magnetic radiation and outputting a second electro-magnetic radiation;
the active optical modulator receiving and modulating the second electro-magnetic radiation and outputting a third electro-magnetic radiation;
the second dispersive element receiving and dispersing the third electro-magnetic radiation and outputting a fourth electro-magnetic radiation; and
the second phase modulator receiving and modulating the fourth electro-magnetic radiation and outputting a fifth electro-magnetic radiation,
the laser radiation being provided based on at least one of:
the first electro-magnetic radiation,
the second electro-magnetic radiation,
the third electro-magnetic radiation,
the fourth electro-magnetic radiation, or
the fifth electro-magnetic radiation.

12. The method of claim 11, wherein the optical cavity further comprises a coupler, and
wherein the method further comprises:
the coupler receiving and splitting the fifth electro-magnetic radiation into a first portion and a second portion, wherein the first portion is output by the coupler as a sixth electro-magnetic radiation, and
wherein the second portion is output by the coupler as the laser radiation.

13. The method of claim 12, wherein the optical cavity further comprises a fixed periodic spectral filter, and
wherein the method further comprises:
the fixed periodic spectral filter receiving and filtering the sixth electro-magnetic radiation and outputting a seventh electro-magnetic radiation,
wherein the first electro-magnetic radiation comprises the seventh electro-magnetic radiation.

14. The method of claim 13, further comprising:
the first phase modulator being controlled by a first control signal,
wherein the first control signal has a first state that causes the first phase modulator to spectrally broaden the second electro-magnetic radiation and a second state opposite the first state that causes the first phase modulator to spectrally narrow the second electro-magnetic radiation, and
the second phase modulator being controlled by a second control signal,
wherein the second control signal has a third state that causes the second phase modulator to spectrally broaden the fourth electro-magnetic radiation and a fourth state opposite the third state that causes the second phase modulator to spectrally narrow the fourth electro-magnetic radiation.

15. The method of claim 14, wherein the seventh electro-magnetic radiation output by the fixed periodic spectral filter comprises a plurality of spectral lines including a particular spectral line,
wherein the method further comprises:
when the first control signal is in the first state, the first phase modulator spectrally broadening the particular spectral line, and
when the second control signal is in the fourth state, the second phase modulator spectrally narrowing the particular spectral line.

16. The method of claim 15, further comprising:
the fixed periodic spectral filter receiving and filtering the particular spectral line based on the particular spectral line being spectrally narrowed by the second phase modulator.

17. The method of claim 16, wherein the particular spectral line travels from the first phase modulator and reaches the second phase modulator after a delay time,
wherein the particular spectral line has a particular wavelength, and
wherein the delay time between the first control signal and the second control signal is based on selecting the particular spectral line having the particular wavelength.

18. The method of claim 17, wherein the delay time between the first control signal and the second control signal is changed to another delay time to select another spectral line of the plurality of spectral lines,
wherein the other spectral line has another wavelength different from the particular wavelength.

19. The method of claim 18, further comprising:
the fixed periodic spectral filter receiving and filtering the other spectral line based on the other spectral line being spectrally narrowed by the second phase modulator.

20. The method of claim 11, wherein the laser further comprises an optical amplifier which receives an input electro-magnetic radiation and emits an output electro-magnetic radiation,
wherein the output electro-magnetic radiation comprises at least one of a source electro-magnetic radiation or an amplification of the input electro-magnetic radiation, and
wherein the output electro-magnetic radiation is combined with at least one of:
the first electro-magnetic radiation,
the second electro-magnetic radiation,
the third electro-magnetic radiation,
the fourth electro-magnetic radiation, or
the fifth electro-magnetic radiation.

* * * * *